United States Patent [19]

Williams et al.

[11] Patent Number: 5,155,048
[45] Date of Patent: Oct. 13, 1992

[54] ORGANIC REAGENT FOR THE COLORIMETRIC DETECTION OF CHLORINE AND OZONE IN DRINKING WATER

[75] Inventors: Roy L. Williams; Sherry L. Williams, both of Newport News, Va.

[73] Assignee: Center for Innovative Technology, Herndon, Va.

[21] Appl. No.: 672,399

[22] Filed: Mar. 20, 1991

[51] Int. Cl.$^5$ .................... G01N 21/00; G01N 21/75
[52] U.S. Cl. .................... 436/164; 436/124; 436/135
[58] Field of Search .................... 436/124, 135, 164

[56] References Cited

U.S. PATENT DOCUMENTS 4,938,926  7/1990  Reiss .................... 422/58

FOREIGN PATENT DOCUMENTS 0027250  2/1984  Japan .

OTHER PUBLICATIONS

Lennard et al., "Unsaturated Amines, IX Through Bis-- Enamines to Aromatics," J. Org. Chem., 21:1188-89 (1956).

Moreau-Houcha et al., "Arynic and SNAr Reactions of Ployfluorobenzenes-Vl," Tetrahedron, 955-959 (1977).

Watanbe et al., "The Facile Synthesis of N-Substituted Piperdines from Glutaraldehyed and Primary Amines with Tetracarbonylhydridoferrate," Chem. Soc. of Japan, 49, 2302-05 (1976).

Rus. Acad. of Sci., 10, 6 VI (1973).

Standard Methods for the Examination of Water and Waste Water 17th Ed., "4500-Cl Chlorine" (Residual).

Primary Examiner—James C. Housel
Assistant Examiner—David Redding
Attorney, Agent, or Firm—Whitham & Marhoefer

[57] ABSTRACT

Para-substituted phenylene ring compounds where the substituent moieties are selected from the group consisting of aminoalkyl rings and alkyl rings, such as 1,1'-para-phenylene dipiperidine and 1,1'-para-phenylene dipyrolidine, can be used as colorimetric reagents for detecting the presence of small quantities of chlorine or ozone in water.

33 Claims, 7 Drawing Sheets

ORGANIC REAGENT FOR THE COLORIMETRIC DETECTION OF CHLORINE AND OZONE IN DRINKING WATER

BACKGROUND OF THE INVENTION

1. Field of the Invention

The present invention is generally related to a method for detecting small quantities of chlorine and ozone in water. More particularly, to using the hydrochloride salt of a para-substituted phenylene ring compound where the substituent moieties are selected from the group consisting of aminoalkyl rings and alkyl rings as a colorimetric reagent for detecting the presence of small quantities of chlorine or ozone in water. Still more particularly, to using the hydrochloride salt of compounds such as 1,1'-para-phenylene dipiperidine and 1,1'-para-phenylene dipyrolidine as colorimetric reagents.

2. Description of the Prior Art

Chlorine and chlorine dioxide are commonly used as disinfectants in the treatment of potable water supplies. Ozone is sometimes employed as a chemical oxidant for removing various constituents from water. For example, manganese, cyanide ion, sulfide ion, and nitrite ion can all be removed with ozone. Ozone is not normally used as a disinfectant because of its short half life in water. In addition, ozone produces oxygen as it decomposes which aerates the water and may actually enhance the potential for regrowth of microorganisms. For this reason, ozone oxidation treatment of a water sample is usually followed by the addition of small quantities of chlorine or chlorine dioxide for disinfecting purposes.

The presence of either residual chlorine or ozone in drinking water poses particular health risks. The Environmental Protection Agency (EPA) will be promulgating standards which limit the residual amount of chlorine and ozone which can be present in drinking water. Several methods have been developed for determining the amount of chlorine in solution. For example, the presence of chlorine is determinable using ultraviolet, continuous amperometric titration, iodometric, colorimetric, and electrode methods. Some methods are specific for free chlorine ($Cl_2$, HOCl, and OCl anion) while others measure total chlorine (free chlorine plus chloramines and organically bound chlorine).

In the ultraviolet (UV) methods, chlorine is detected by absorption in the UV range. This method is only suitable for qualitative measurements because the molar absorptivities of the chlorine and chloramine species are quite low. The continuous amperometric titration method is considered a standard for routine laboratory measurements. However, a more experienced analyst and extremely clean working conditions are required for conducting a continuous amperometric titration. It has also been found there are statistically significant differences between the results obtained using membrane electrodes (electrode method) and the results obtained by amperometric titration. It is possible that the membrane electrodes provide a free chlorine reading, while the amperometric electrodes measure the sum of free and organically combined chlorine. In the iodometric titration, high concentrations of total chlorine are measurable.

Because of their ease of use, colorimetric methods are preferred for measuring chlorine. N-N-diethyl-p-phenylene diamine sulfate, or DPD salt, which is available from LaMotte Chemical Products Co. or the HACH Co., is the most widely used colorimetric reagent for measuring chlorine on the market. Very low levels as well as high levels of chlorine are quantifiably determinable using DPD. Syringaldazine, commonly known as "FACTS", is another colorimetric reagent for determining the chlorine concentration in solution. The results achievable with FACTS are comparable to the widely accepted DPD test. However, the major disadvantage with FACTS is the difficulty in dissolving syringaldazine. Both FACTS and DPD operate on non-reversible reaction principles, i.e., each requires an oxidative step which produces a colored product that is measured. Both FACTS and DPD tests must be conducted under controlled pH conditions.

Leuco crystal violet (LCV), which has the chemical formula 4,4,4-methyldynetris-(N,N-dimethylaniline), is yet another chemical used for the determination of chlorine in drinking water. This method is capable of determining all of the chloramines as well as free chlorine. The precision of LCV is equivalent to other colorimetric methods, such as DPD and FACTS.

Both the DPD and amperometric titration methods for measuring free available chlorine are subject to interference from monochloramine and dichloramine. The measured free available chlorine concentration in the presence of chloramines is often significantly larger than the true free available chlorine residual. Interference of chloramines can be reduced when using the DPD method by executing rapid titrations. In addition, it has been found that it is beneficial to add small quantities of thioacetamide to the solution when using DPD to test for free chlorine. Mercuric chloride is also known to minimize the affect of chloramines on the free chlorine measurement when testing by DPD. Chloramine interference in the amperometric titration can be reduced by maintaining a 200 millivolt positive potential on the platinum electrode.

Presently, the recommended method for detecting residual ozone in solution is by the use of the Indigo trisulfonate reagent. This method is based on a measure of the decolorization of the indigo blue color by ozone. The Indigo method is rapid and stoichiometric.

Both DPD and FACTS can also be used to detect ozone. However, the accuracy obtainable when testing for ozone with these reagents may be impaired by the presence of other highly oxidative reactants in solution, i.e., all oxidants capable of oxidizing iodide ion such as halogens, manganese oxides and ozone decomposition byproducts. Generally, other colorimetric methods are more reliable for ozone detection.

Therefore, a need exists for reagents which can detect low levels of chlorine or ozone, and which are less subject to chloramine or other oxidizing agent interferences. In addition, a need exists for reagents which are easier to handle and do not require buffering the solution under test.

SUMMARY OF THE INVENTION

It is therefore an object of the present invention to provide a method of using parasubstituted phenylene ring compounds, such as 1,1'-para-phenylene dipiperidine and 1,1'-para-phenylene dipyrolidine, as colorimetric reagents for quantifiably detecting low levels of chlorine or ozone in water solutions such as drinking water or waste water.

According to the invention, para substituted phenylene ring compounds where the substituent moieties are selected from the group consisting of aminoalkyl rings and alkyl rings, such as 1,1'-para-phenylene dipiperidine and 1,1'-para-phenylene dipyrolidine, have been prepared from 1,4-cyclohexanedione (commonly called tetrahydroquinone) following the procedure of Maddox for the synthesis of the drug PCP. The compound's structure was characterized using classical analytical methods, i.e., C, H, N analysis, and using modern spectral techniques, i.e., infra-red (IR) and nuclear magnetic resonance (NMR) spectroscopy. Both 1,1'-para-phenylene dipiperidine and 1,1'-para-phenylene dipyrolidine have been described previously in the literature (see, for example Leonard et al., *J. Org. Chem.*, 21:1188–89 (1956)), but they have not been utilized for the detection of either chlorine or ozone in water. These compounds constitute analogs of N,N,N',N'-tetramethyl phenylene diamine known as Wuster's salt. Conversion of these compounds to their hydrochloride salts enhances solubility.

The applicant's found that compounds such as 1,1'-para-phenylene dipiperidine and 1,1'-para-phenylene dipyrolidine can produce a quantifiable blue color when reacted in a fluid containing low levels of either chlorine or ozone. In addition, chloramines do not adversely affect measurements for free available chlorine in solution at levels of 0.5–20.0 parts per million (ppm) within the normal measurement time of 1–2 minutes. 1,1'-para-phenylene dipiperidine can be used to detect ozone residuals within a range of 0.1 to 2.4 parts per million (ppm) with the production of a blue color. Hydrogen peroxide, one of the major byproducts of ozonization and a significant oxidant, does not affect the operation of these reagents with regard to ozone detection even at levels exceeding 2000 ppm.

BRIEF DESCRIPTION OF THE DRAWINGS

The foregoing and other objects, aspects and advantages will be better understood from the following detailed description of the preferred embodiment of the invention with reference to the drawings, in which.

DETAILED DESCRIPTION OF A PREFERRED EMBODIMENT OF THE INVENTION

Figure 1:
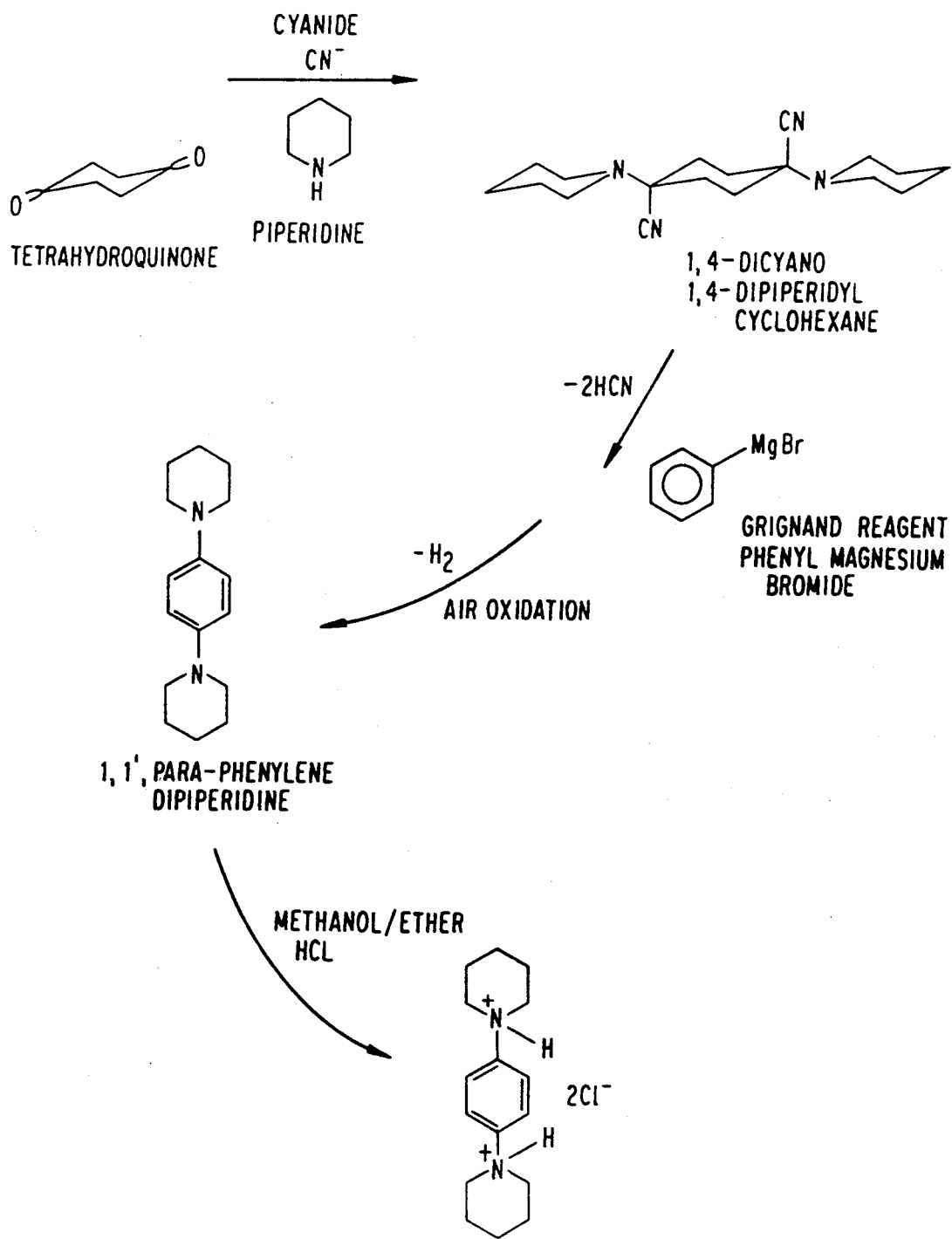
FIG. 1 is a schematic diagram showing the synthetic route used for preparing the hydrochloride salt of 1,1'-para-phenylene dipiperidine.

Referring now to the drawings, and more particularly to FIG. 1, there is shown the synthesis route for preparing the dihydrochloride salt of 1,1'-para-phenylene dipiperidine. The synthesis involves the reaction between cyanide ion, piperidine, and tetrahydroquinone. The resulting yield of 1,4-dicyano-1,4-dipiperidylcyclohexane is approximately 80%. Tetrahydroquinone, cyanide, and piperidine are commercially available from Aldrich Chemical Co. Piperidine can only be obtained in compliance with federal drug enforcement law. The 1,4-dicyano-1,4-dipiperidylcyclohexane is then reacted with a Grignard reagent, phenyl magnesium bromide, which is also available from Aldrich Chemical Co. In this reaction, the Grignard reaction may cause decyanation of the dicyano compound to give a dienanmine structure which undergoes air oxidation in solution to produce 1,1'-para-phenylene dipiperidine free base. The yield is approximately 28% for the Grignard reaction. The structure of 1,1'-para-phenylene dipiperidine was confirmed by classical CHN analytical methods and modern spectral techniques such as IR and NMR. The compounds melting point and spectral properties were consistent with those reported in the literature.

1,1'-para-phenylene dipiperidine can also be made by other processes such as those reported in Leonard et al., *J. Org. Chem.*, 21, 1188–89 (1956), Moreau-Hochu et al., *Tetrahedron*, 955–59 (1977), Watanabe et al., *Chem. Soc. of Japan*, 49, 2302–05 (1976), and in *Rus. Acad. Sci.*, 10, 6 VI (1973), and each of these articles are incorporated herein by reference. The synthetic scheme shown in FIG. 1 may provide a superior yield than the others reported in the literature. 1,1'-para-phenylene dipyrolidine and other para-substituted phenylene compounds with aminoalkyl or alkyl rings may also be produced by similar synthetic pathways to those shown in FIG. 1 or in the incorporated articles. The method of using the para-substituted phenylene compounds with aminoalkyl or alkyl rings is independent of the method of their production.

The free base of 1,1'-para-phenylene dipiperidine is water insoluble. Water solubility can be achieved by converting 1,1'-para-phenylene dipiperidine free base to its dihydrochloride salt by reaction with HCl in a diethyl ether-methanol solution. Other salts could also be made for solubilizing the para-substituted phenylene compounds of this invention, such as the dihydrobromide or the disulfate, for example. Some advantages with regard to selectivity and reactivity may be incorporated into the 1,1'-para-phenylene dipiperidine and 1,1'-para-phenylene dipyrolidine species by conversion of the respective free bases into their mono-N-methyl salts.

1,1'-para-phenylene dipiperidine is a unique analog of the class of compounds known as N,N'-dialkyl-p-phenylene-diamines. The experiments reported below show that 1,1'-para-phenylene dipiperidine is superior to other similar substituted para-phenylene diamines such as the N,N'-diethyl-p-phenylene diamine, DPD, in the detection of residual chlorine and ozone in water. It is likely that the mechanism of color production for 1,1'-para-phenylene dipiperidine is the same as that for other para-phenylene diamines and may involve the formation of a transient colored radical cation species during the reaction with chlorine or ozone. 1,1'-para-phenylene dipyrolidine also forms a blue colored species when exposed to low levels of ozone or chlorine. 1,1'-para-phenylene dipiperidine reacts with light, as do most para-phenylene diamines (presumably a photo-oxidation) and, therefore, stock solutions should be stored in the dark prior to use. Crystalline 1,1'-para-phenylene dipiperidine, however, is quite stable and can be stored as the dihydrochloride salt without decolorization.

A series of experiments have been performed to test the accuracy and precision of 1,1'-para-phenylene dipiperidine for detecting chlorine. In the experiments, 1,1'-para-phenylene dipiperidine was present as its dihydrochloride salt which is soluble in water. An IBM Model 9410 UV/Vis spectrophotometer was utilized and the wavelength was set at 615 nm, which is the lambda max for the colored species produced from 1,1'-para-phenylene dipiperidine. Samples to be tested for chlorine concentration were prepared in chlorine demand free water, which is prepared as prescribed in *Standard Methods for the Examination of Water and Waste Water*, 17th ed., chlorine residual section, 4500-Cl The concentration of chlorine in each test sample was determined according to Beer's Law.

Figure 2:
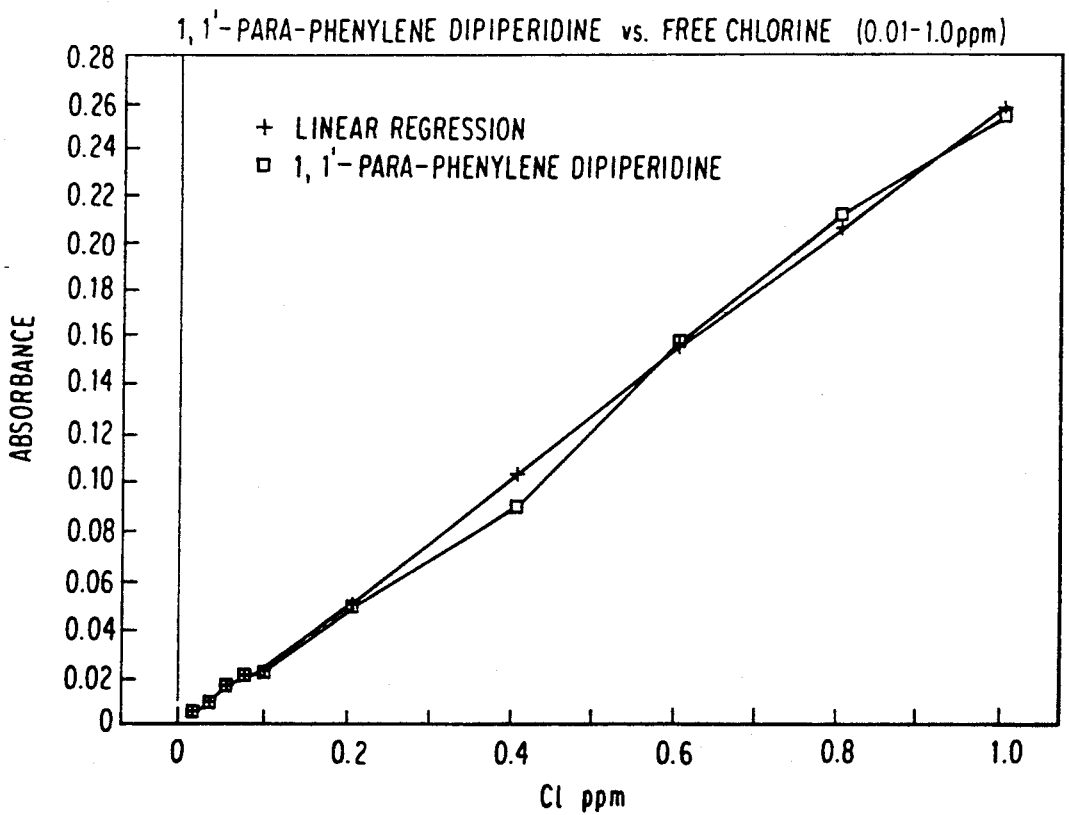
FIG. 2 is a line graph showing that 1,1'-para-phenylene dipiperidine produces a linear absorbance in a UV/Vis spectrophotometer for different concentrations of chlorine from 0.01 ppm to 1 ppm.
Figure 3:
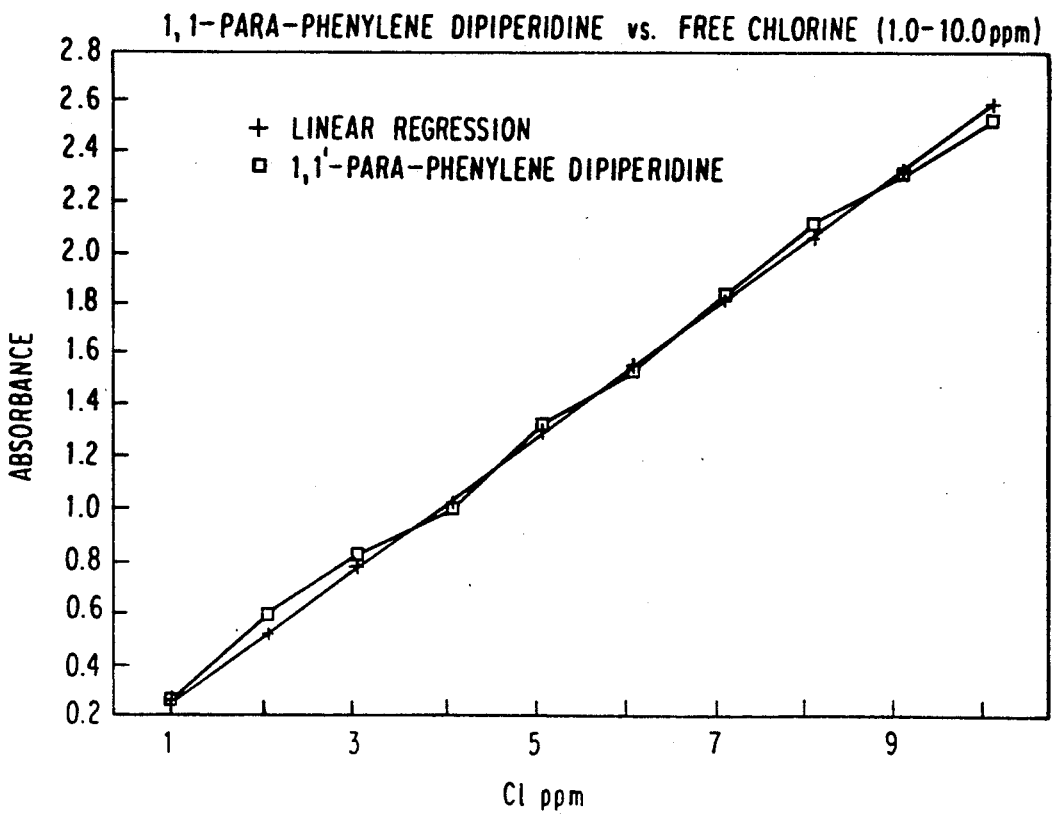
FIG. 3 is a line graph showing that 1,1'-para-phenylene dipiperidine produces a linear absorbance in a UV/Vis spectrophotometer for different concentrations of chlorine from 1.0 ppm to 10.0 ppm.

FIGS. 2 and 3 show a linear relationship between the residual chlorine concentration ($Cl_2$ in mg/L) in solution and the absorbance measured when 1,1'-para-phenylene dipiperidine is used as the chlorine detecting reagent. In this experiment, 1,1'-para-phenylene dipiperidine is present at a concentration of 10 mg/50 ml (200 mg/L). In FIGS. 2 and 3, the actual absorbance measurements for particular samples are indicated by points designated as boxes and points which correspond to the statistically derived line are indicated as crosses. The linear relationship has a correlation coefficient (R) of 0.988505 which is considered statistically significant according to normal quality control evaluation methods. From FIGS. 2 and 3, it can be seen that the practical working range for the detection of free residual chlorine in drinking water using 1,1'-para-phenylene dipiperidine was found to be 0.01 to 10.0 mg/L which places 1,1'-para-phenylene dipiperidine within the same detection range as other colorimetric reagents such as DPD, FACTS and LCV. Using higher concentrations of 1,1'-para-phenylene dipiperidine in solution may allow detecting even smaller quantities of free residual chlorine.

Figure 4:
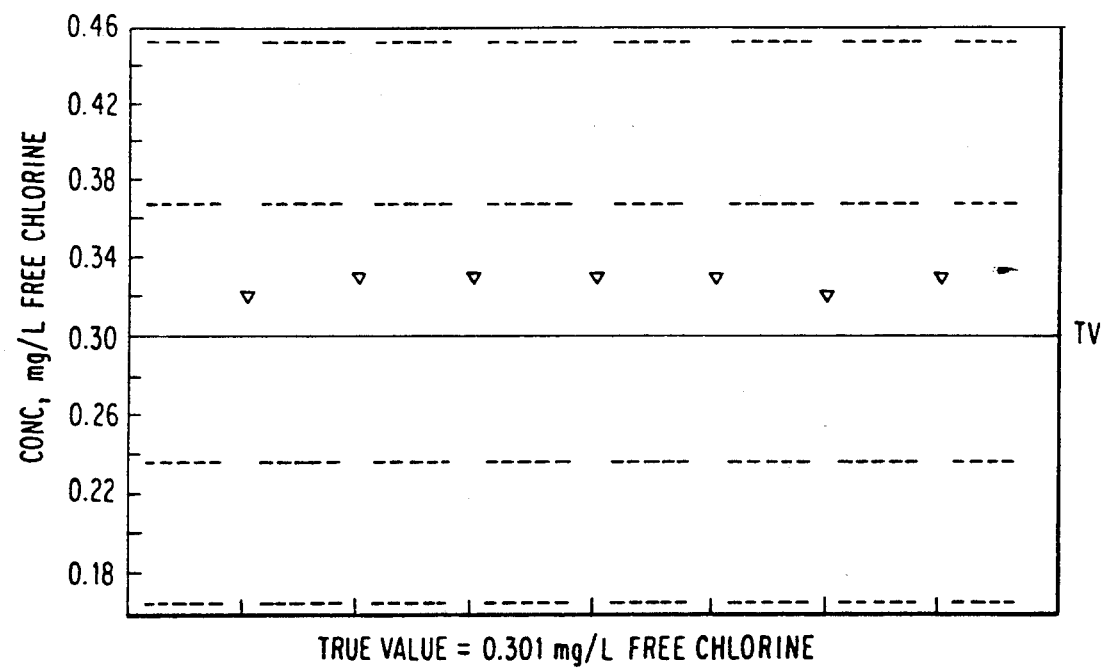
FIGS. 4 and 5 are bar graphs showing that 1,1'-para-phenylene dipiperidine can detect small quantities of free chlorine in standard EPA preparations with a high degree of precision and accuracy.
Figure 5:
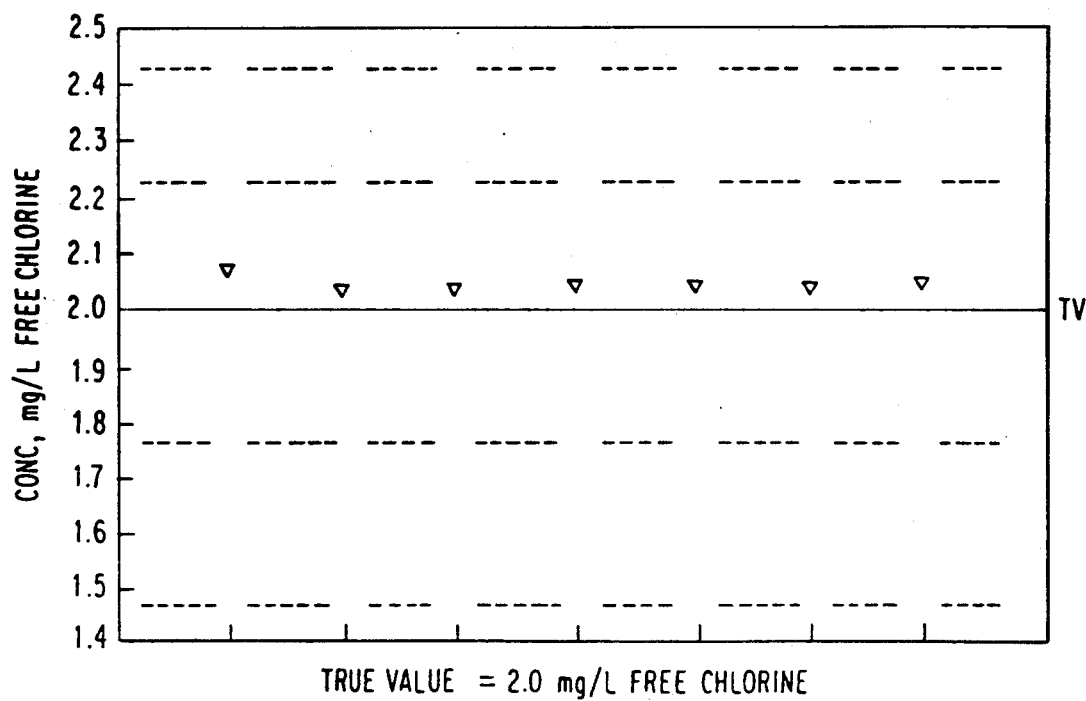

FIGS. 4 and 5 show the results of experiments designed to test the precision and accuracy of 1,1'-para-phenylene dipiperidine in detecting free chlorine. Performance standards, which are available from the Environmental Protection Agency (EPA) and which contain known amounts of residual chlorine, are tested seven times each with a 10 mg/50 ml (200 mg/L) solution of 1,1'-para-phenylene dipiperidine. The results for the performance standard containing 0.301 mg/L free chlorine, shown in FIG. 4, indicate that all seven measurements fell slightly above a 0.301 mg/L chlorine reading, but all were within one standard deviation of the parameters set by the EPA. FIG. 5 shows that at a higher concentration of free chlorine, i.e., 2.0 mg/L, the accuracy and precision of the 1,1'-para-phenylene dipiperidine reagent was even better.

Figure 6:
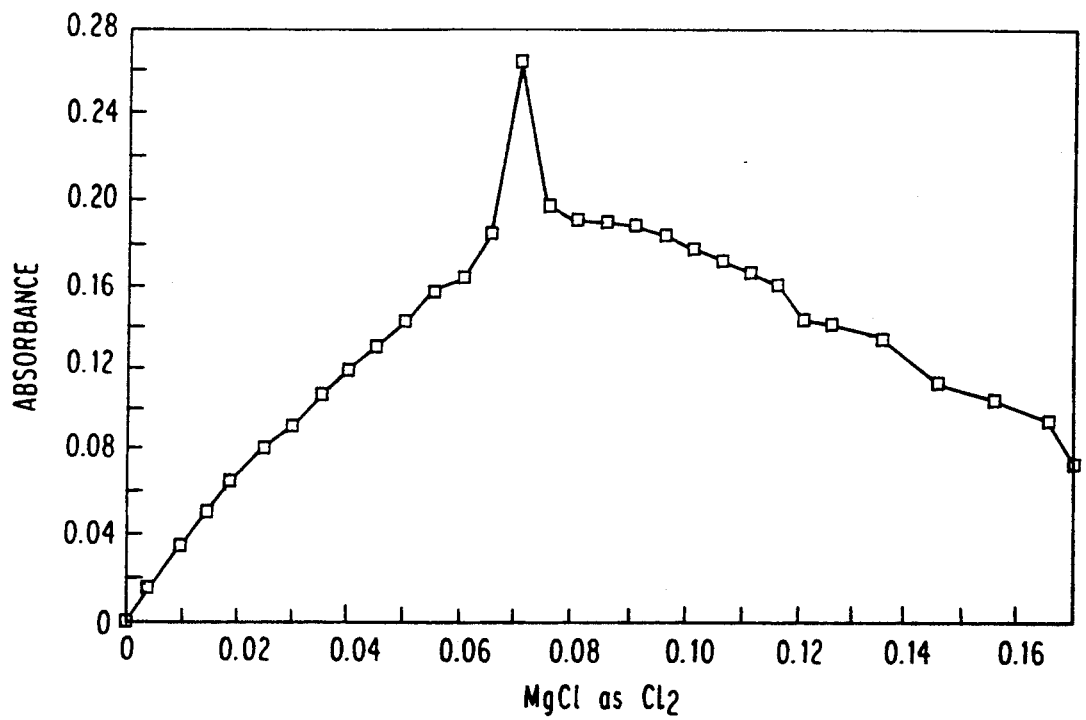
FIG. 6 is a line graph showing the results of titrating a 1,1'-para-phenylene dipiperidine solution with an aqueous chlorine solution.

FIG. 6 shows the results of a colorimetric titration of 1,1'-para-phenylene dipiperidine where a 1 mg/L sample of 1,1'-para-phenylene dipiperidine was titrated with a 1 mg/L standardized solution of chlorine. During the titration, the absorbance as well as the pH of the mixture is carefully monitored. As shown in FIG. 6, there is a linear increase in absorbance of the sample as the chlorine solution is slowly added. The maximum absorbance is achieved after the addition of 78 ml. of the 1 mg/L chlorine titrant. This value of titrant corresponds to one equivalent of available chlorine and suggests that the reaction between 1,1'-para-phenylene dipiperidine and chlorine is a 1:1 reaction. At the equivalence point, the sample exhibited a maximum absorbance of 0.262. The pH during this period is observed to rise from 5.35 to 5.86. As more titrant is added, there is a decrease of absorbance to 0.073. The pH of the resulting solution is 6.0.

Figure 7:
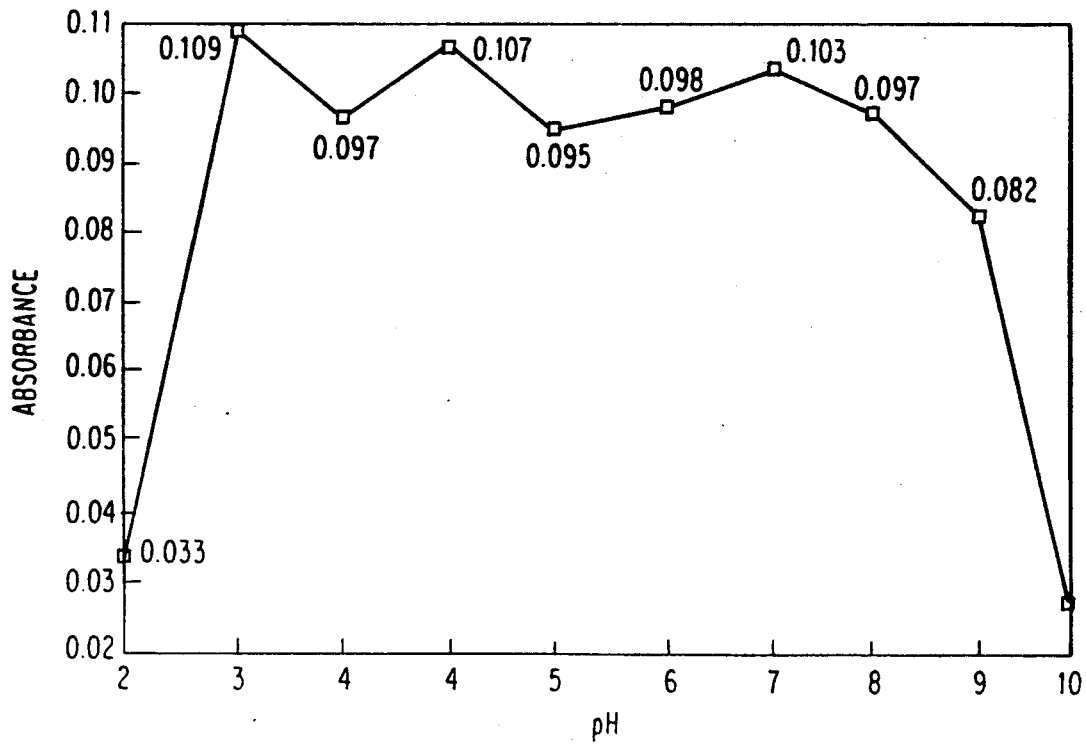
FIG. 7 is a line graph showing that 1,1'-para-phenylene dipiperidine can accurately detect quantities of chlorine even when the pH is varied.

FIG. 7 shows that 1,1'-para-phenylene dipiperidine can accurately detect chlorine at different pH levels. In the experiments, several samples, each of which contained a 1 mg/L solution of chlorine, were adjusted to the desired pH (between 2 and 11) using sulfuric acid to lower the pH and using sodium hydroxide to raise the pH. Each sample was then treated with 1,1'-para-phenylene dipiperidine at 10 mg/50 ml (200 mg/L) and the absorbance was immediately recorded. From FIG. 7 it can be seen that 1,1'-para-phenylene dipiperidine accurately detected the 1 mg/L concentration of chlorine in solutions which ranged in pH from 3 to 9. This data may be interpreted to suggest that 1,1'-para-phenylene dipiperidine buffers itself in solution. The wide range of pH utility for 1,1'-para-phenylene dipiperidine is a significant advantage over DPD and FACTS which must be buffered properly by other constituents to render accurate results.

Figure 8A:
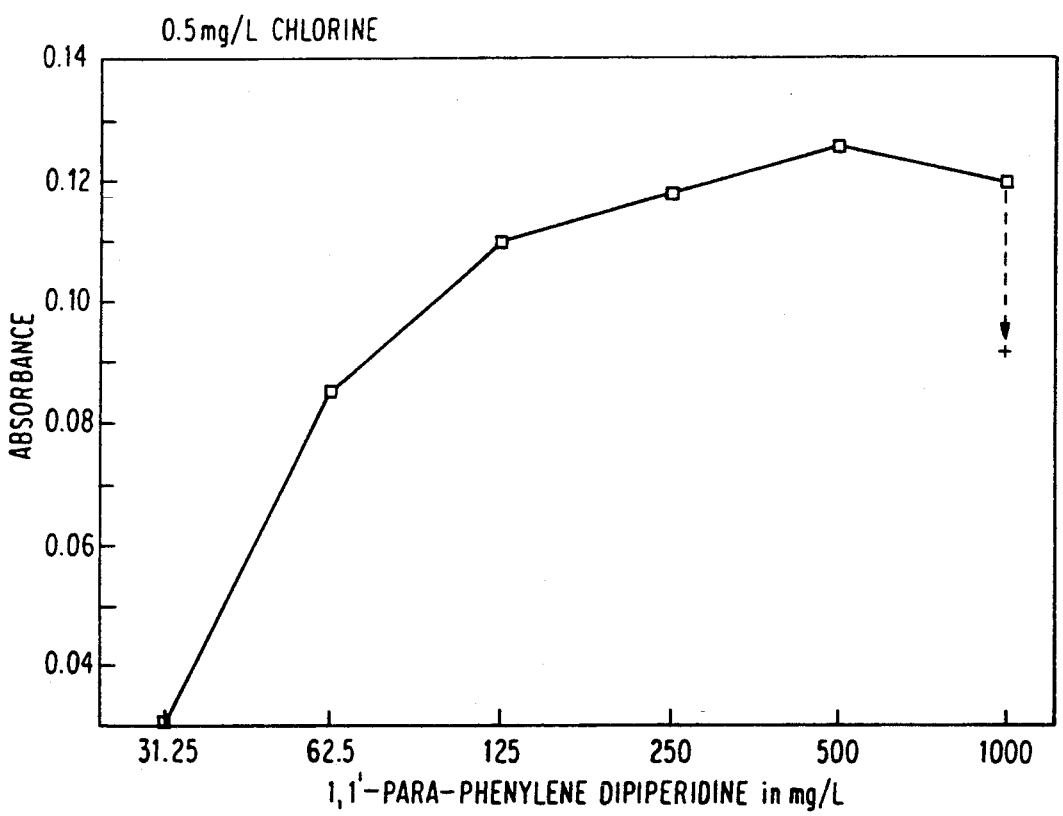
FIGS. 8a and 8b are graphs showing the absorbance enhancement produced when increasing concentrations of 1,1'-para-phenylene dipiperidine are used to detect free chlorine.
Figure 8B:
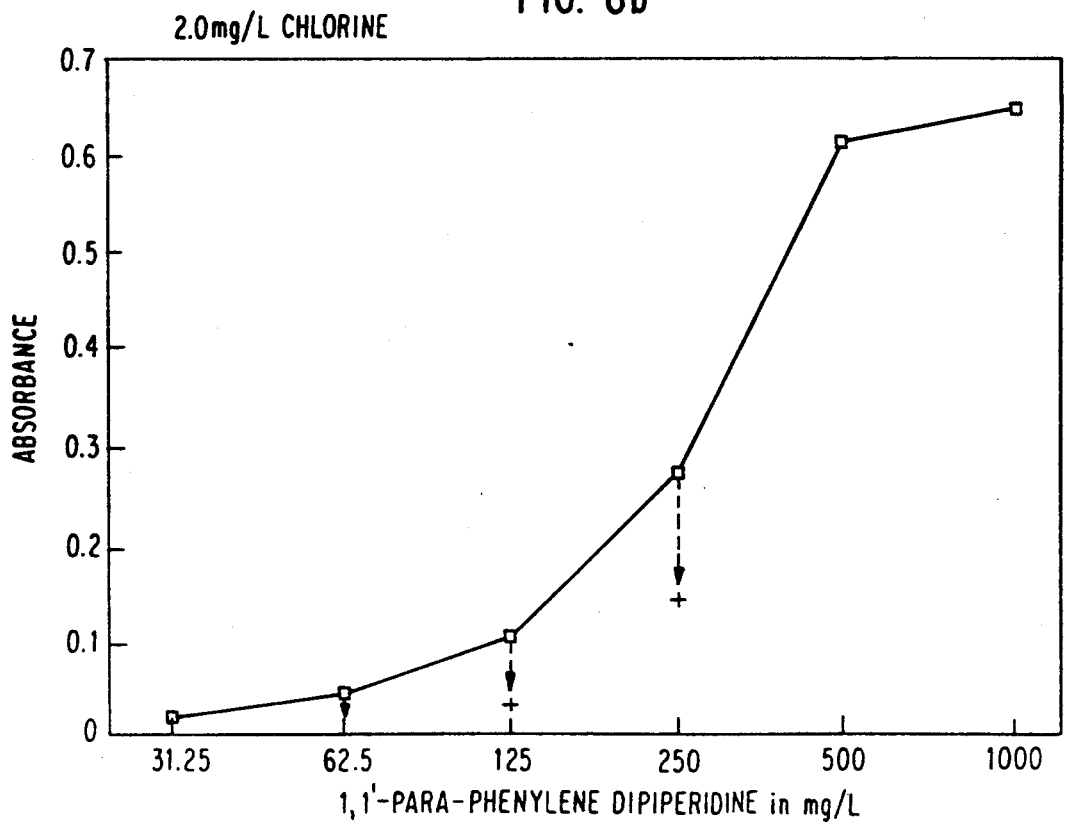

FIGS. 8a and 8b show the results of experiments where varying concentrations of 1,1'-para-phenylene dipiperidine are used to test for free chlorine in solution. Two chlorine test samples are prepared with one test sample containing 0.5 mg/L free chlorine and the other test sample containing 2.0 mg/L free chlorine. These test samples are prepared using chlorine free water according to standard laboratory techniques. Several 1,1'-para-phenylene dipiperidine samples are prepared where the concentrations of the samples is varied between 31.25 mg/L and 1000 mg/L 1,1'-para-phenylene dipiperidine. In particular, the concentration of the 1,1'-para-phenylene dipiperidine samples are the following: 31.25 mg/L, 62.5 mg/L, 125 mg/L, 250 mg/L, 500 mg/L, and 1000 mg/L. Each chlorine test sample is then combined with each of the 1,1'-para-phenylene dipiperidine samples and the resulting absorbance is measured in a UV spectrophotometer set at 615 nm.

In FIGS. 8a and 8b, the square boxes indicate the absorbance measured the first few minutes after combining the chlorine sample with the 1,1'-para-phenylene dipiperidine sample and the crosses indicate the absorbance measured more than ten minutes after combining the reagent with the chlorine test solution. FIG. 8a shows that the absorbance produced by the reaction of 0.5 mg/L chlorine increases as the 1,1'-para-phenylene dipiperidine concentration increases up to 500 mg/L. At higher concentrations, i.e., 1000 mg/L, the absorbance declines. In addition, the absorbance measurements for the lower concentrations of 1,1'-para-phenylene dipiperidine are stable after ten minutes while the measurement for the higher concentration 1,1'-para-phenylene dipiperidine declines with time. FIG. 8b shows that the absorbance produced by the reaction of 2.0 mg/L chlorine also increases as the 1,1'-para-phenylene dipiperidine concentration increases. Unlike the time stability response shown in FIG. 8a, FIG. 8b shows that the absorbance measured with higher concentrations of 1,1'-para-phenylene dipiperidine is stable for longer periods of time than the absorbance measured with lower concentrations of 1,1'-para-phenylene dipiperidine. From FIGS. 8a and 8b, it can be seen that the optimum concentration of the 1,1'-para-phenylene dipiperidine reagent is approximately 500 mg/L. This conclusion is based on the fact that a greater sensitivity is achievable when greater absorbencies can be measured. As was shown above in conjunction with FIGS. 2-5, lower concentrations of 1,1'-para-phenylene dipiperidine can also produce accurate results (i.e., in those experiments a 10 mg/ 50 ml solution of 1,1'-para-phenylene dipiperidine is used which is 200 mg/L). Only a few minutes is required to perform the 1,1'-para-phenylene dipiperidine test; hence, any instability of the solution under test over long periods of time does not pose serious problems.

Experiments have also been performed which show that 1,1'-para-phenylene dipiperidine specifically measures free available chlorine, which is comprised of $Cl_2$, HOCl, and OCl anion, and does not measure total available chlorine, which is the sum of the free available chlorine and organic chlorine constituents such as monochloramine ($NH_2Cl$) and dichloramine ($NHCl_2$). The ability to distinguish free available chlorine from total available chlorine is the result of 1,1'-para-phenylene dipiperidine reacting with free available chlorine at a much faster rate than it reacts with monochloramine or dichloramine. The ability to specifically identify free available chlorine is a particular advantage because the free available chlorine measurement is the more accurate indicator of the microbiological quality of the treated water. The chloramines are poorer disinfectants and their contributions to the total chlorine measurement may contribute to an inaccurate reading of the available disinfection potential of the finished water.

Figure 9:
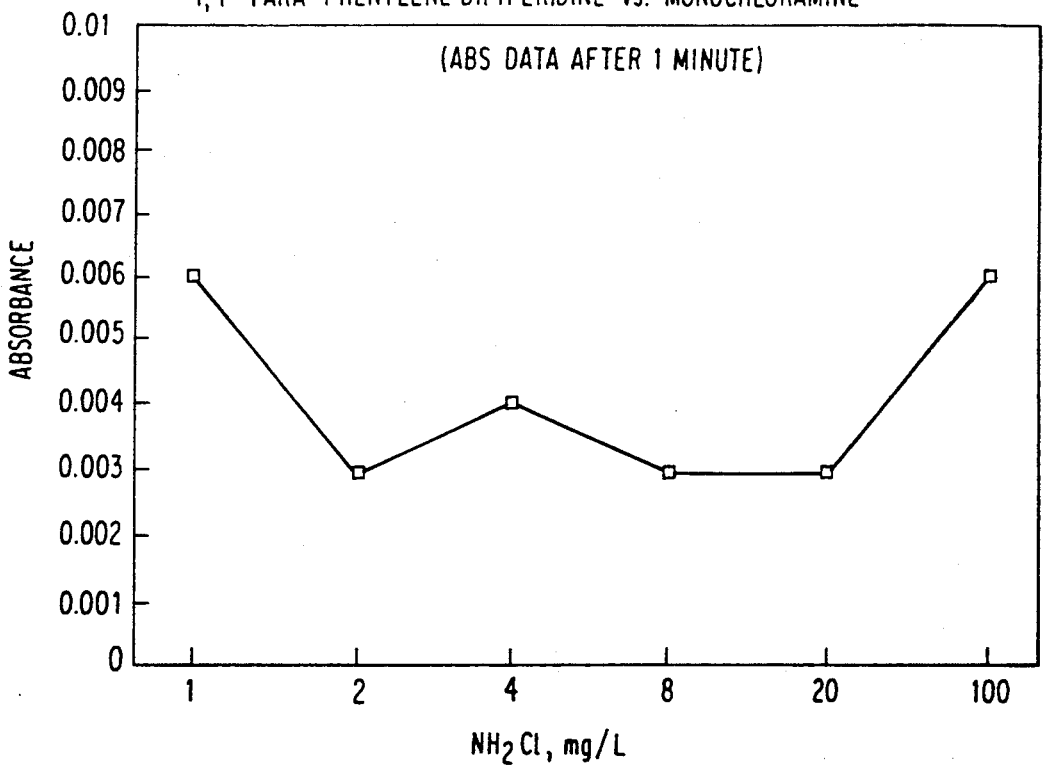
FIG. 9 is a graph showing that the absorbance measurement produced when varying concentrations of monochloramine is mixed with 500 mg/L 1,1'-para-phenylene dipiperidine is minimal.

FIG. 9 shows the results of an experiment testing the responsiveness of 1,1'-para-phenylene dipiperidine to a sample containing monochloramine ($NH_2Cl$). Six test samples containing varying concentrations of $NH_2Cl$ are prepared; specifically, these test samples contain 1, 2, 4, 8, 20, and 100 mg/L $NH_2Cl$. Each of these test samples are then combined in a mixture containing 500 mg/L 1,1'-para-phenylene dipiperidine. Approximately one minute after forming a mixture of the monochloramine and the 1,1'-para-phenylene dipiperidine, the absorbance of the mixture is measured using a spectrophotometer set at 615 nm. FIG. 9 shows that the absorbance measured for all the samples is less than 0.007. Therefore, it can be concluded that the presence of $NH_2Cl$, even at extremely large concentrations (i.e., 100 mg/L), has little affect on the chlorine measurement.

In all cases, there is a gradual development of a pale blue color. Therefore, it may be concluded that 1,1'-para-phenylene dipiperidine reacts with available free chlorine at a much more rapid rate than with monochloramine. Since absorbance measurements with 1,1'-para-phenylene dipiperidine are intended to be made soon after mixing with a test sample, the slow reaction of monochloramine with 1,1'-para-phenylene dipiperidine will not adversely affect a free chlorine measurement. If one simply wanted to detect the presence of monochloramine in a solution which was known not to contain free chlorine, 1,1'-para-phenylene dipiperidine, by its slow development of a blue color, could be used.

Figure 10:
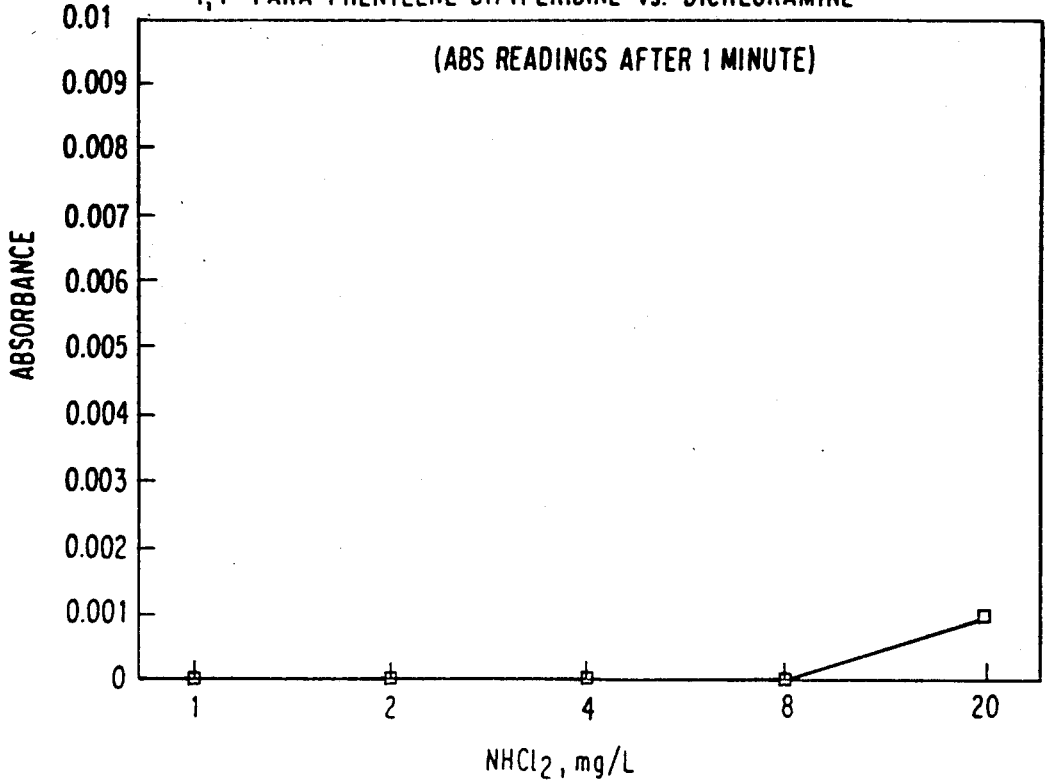
FIG. 10 is a graph showing that the absorbance measurement produced when varying concentrations of dichloramine is mixed with 500 mg/L 1,1'-para-phenylene dipiperidine is minimal.

FIG. 10 shows the results of a similar experiment to that described above in conjunction with FIG. 9. In particular, the responsiveness of 1,1'-para-phenylene dipiperidine to samples containing dichloramine is measured. Five test samples containing varying concentrations of $NHCl_2$ are prepared and these samples contain 1, 2, 4, 8, and 20 mg/L $NHCl_2$. Each of these test samples are then combined in a mixture containing 500 mg/L 1,1'-para-phenylene dipiperidine. Approximately one minute after forming a mixture of the dichloramine and the 1,1'-para-phenylene dipiperidine, the absorbance of the mixture is measured using a spectrophotometer set at 615 nm. FIG. 10 shows that the absorbance measured for all the samples is less than 0.002. No change in color occurred for over thirty minutes; therefore, it can be concluded that the presence of $NHCl_2$ has little affect on the free chlorine measurement. To check the results shown in FIG. 10, after thirty minutes, the solutions of dichloramine and 1,1'-para-phenylene dipiperidine are treated with tap water which produces an immediate blue color indicative of 2-3 mg/L of residual chlorine. Hence, it is clear that the 1,1'-para-phenylene dipiperidine is active, it is just not reactive with dichloramine.

Experiments have been conducted which show that 1,1'-para-phenylene dipiperidine is capable of detecting residual ozone levels in water. The ozone reacts rapidly with 1,1'-para-phenylene dipiperidine to produce the same absorption pattern as does chlorine, and the lambda max for the species produced by the reaction of ozone with 1,1'-para-phenylene dipiperidine is 615 nm. In contrast to other colorimetric reagents for the detection of residual chlorine and ozone, 1,1'-para-phenylene dipiperidine does not require the use of potassium iodide to produce the colorimetric reaction and provides a direct method for residual detection.

Figure 11:
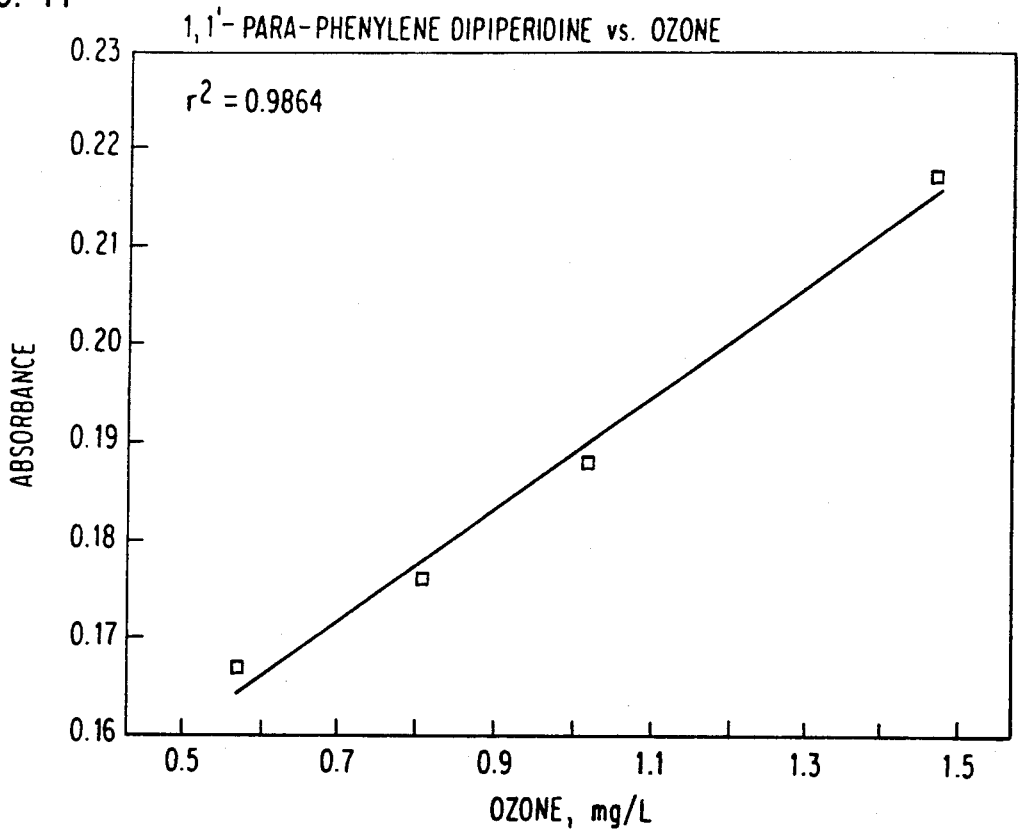
FIGS. 11 and 12 are graphs showing the linear absorbance response for varying concentrations of 1,1'-para-phenylene dipiperidine with respect to increasing quantities of ozone.
Figure 12:
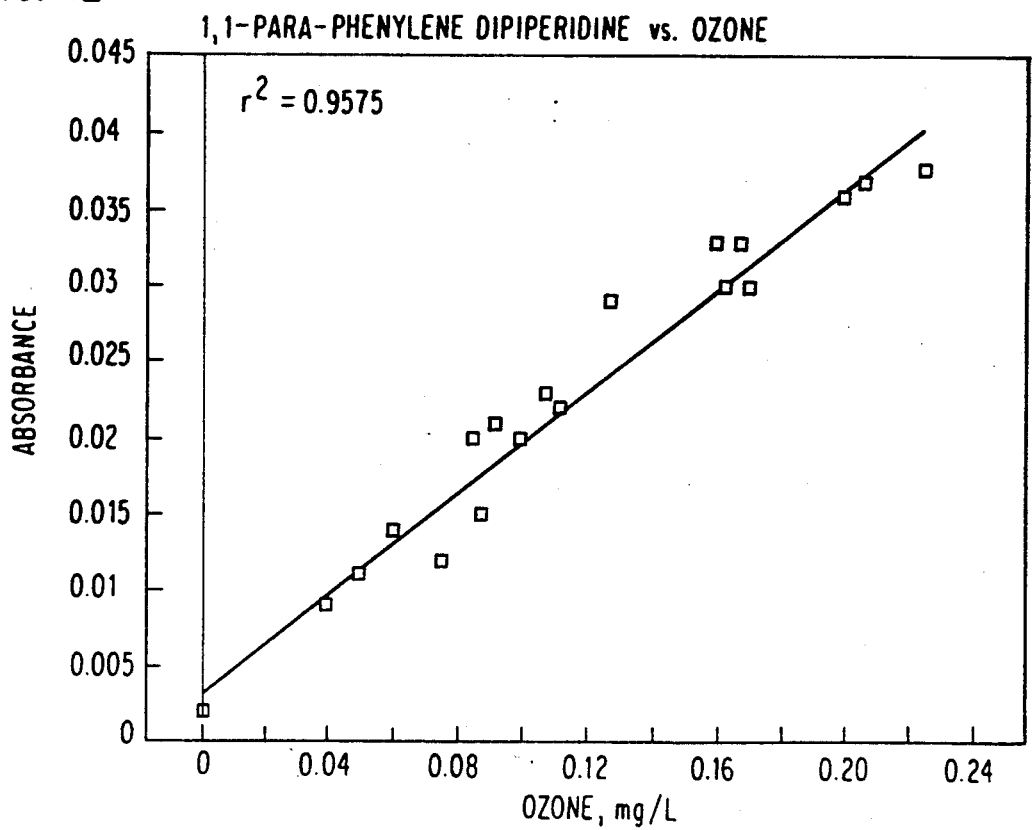

FIGS. 11 and 12 show the measured absorbance obtained when 200 mg/L of the dihydrochloride salt of 1,1'-para-phenylene dipiperidine is reacted with water samples containing increasing concentrations of ozone. FIG. 11 shows a linear response for higher ozone doses, e.g., 0.5-1.5 ppm ozone, and FIG. 12 shows a linear response for low levels of ozone, e.g., 0.04-0.24 ppm ozone. The curves shown in FIGS. 11 and 12 each have a correlation factor greater than 0.95. The failure of the 1,1'-para-phenylene dipiperidine graphs to pass through zero is due to some degree of fading. This fading process may be due to the subsequent reaction of the colored radical cation species with more ozone. Conversion of the 1,1'-para-phenylene dipiperidine and 1,1'-para-phenylene dipyrolidine free bases to a suitable mono-N-alkyl salt (as opposed to the dihydrochloride salt as was done in these experiments) may eliminate this problem and enhance the sensitivity of the system to ozone residual detection. The linear response of 1,1'-para-phenylene dipiperidine alone makes it suitable for making quantitative measurements for solutions containing low levels of ozone, e.g., monitoring low levels of ozone can be accomplished by establishing a standard curve and comparing the absorbance obtained for a test sample with the standard curve.

A qualitative experiment has been conducted which demonstrates that the response of 1,1'-para-phenylene dipiperidine to ozone in solution is not affected by other oxidants such as hydrogen peroxide. 1,1'-para-phenylene dipiperidine is added to a 2000 mg/L sample of $H_2O_2$ at pH 7 and no color change occurs. Adding tap water to the $H_2O_2$/1,1'-para-phenylene dipiperidine solution results in a brilliant blue color, thereby indicating 1,1'-para-phenylene dipiperidine is still active. As discussed above in conjunction with FIG. 11, adding 1,1'-para-phenylene dipiperidine to a chlorine free water solution containing low levels of ozone results in a brilliant blue color.

While the above experiments were conducted primarily with 1,1'-para-phenylene dipiperidine, 1,1'-para-phenylene dipyrolidine has been prepared and also results in a blue color when exposed to low levels of chlorine or ozone. Likewise, it can be expected that para-substituted phenylene compounds with five membered aminoalkyl and alkyl ring substituents could also produce similar results. Although the above experiments were conducted using a UV/Vis spectrophotometer, the use of the para-substituted phenylene compounds with aminoalkyl and alkyl ring substituents is adaptable to a variety of other detection methods. For example, the compounds could be used in a field test application where the analyst uses a color comparator. Pre-measured kits could be supplied for field use. In addition, chlorine or ozone concentration could be determined by visual endpoint detection. The time frame for detection is less than 1 min.

While the invention has been described in terms of its preferred embodiment wherein para-substituted phenylene compounds with aminoalkyl or alkyl ring substituents are used as reagents in their salt form for the quantifiable detection of low levels of chlorine or ozone in solution, those skilled in the art will recognize that the invention can be practiced with modification within the spirit and scope of the appended claims.

Having thus described our invention, what we claim as new and desire to secure by Letters Patent is as follows:

1. A method of detecting chlorine in a fluid, comprising the steps of solubilizing a para-substituted phenylene ring compound where the substituent moieties are selected from the group consisting of five and six membered aminoalkyl rings and five and six membered alkyl rings in said fluid and monitoring a color change in said fluid.

2. A method as recited in claim 1 wherein said step of monitoring further includes the steps of measuring an intensity of a blue color in said fluid and determining a concentration of chlorine from said intensity.

3. A method as recited in claim 2 wherein said step of measuring is performed detecting light absorption at 615 nm.

4. A method as recited in claim 2 wherein said step of measuring is performed within ten minutes of said step of solubilizing said para substituted ring compound in said fluid such that said concentration of chlorine determined during said step of determining represents a concentration of free available chlorine in said fluid.

5. A method as recited in claim 1 wherein said step of monitoring is performed by comparing a color observed in said fluid with a color chart.

6. A method as recited in claim 1 wherein said para-substituted phenylene ring compound solubilized in said fluid is selected from the group consisting of 1,1'-para-phenylene dipiperidine and 1,1'-para-phenylene dipyrolidine.

7. A method as recited in claim 6 wherein said para-substituted phenylene ring compound has a concentration ranging from 100 milligrams per liter to 1000 milligrams per liter.

8. A method as recited in claim 6 wherein said concentration is approximately 500 milligrams per liter.

9. A method as recited in claim 6 wherein said para-substituted phenylene ring compound is solubilized as a salt.

10. A method as recited in claim 9 wherein said salt is a hydrochloride salt.

11. A method as recited in claim 9 wherein said salt is a mono-N-alkyl salt.

12. A method as recited in claim 6 wherein said step of monitoring includes the steps of measuring an intensity of a blue color in said fluid and determining a concentration of chlorine from said intensity.

13. A method as recited in claim 12 wherein said step of measuring is performed detecting light absorption at 615 nm.

14. A method as recited in claim 12 wherein said step of measuring is performed within ten minutes of said step of solubilizing said para-substituted ring compound in said fluid such that said concentration of chlorine determined during said step of determining represents a concentration of free available chlorine in said fluid.

15. A method as recited in claim 12 wherein said concentration of chlorine ranges from 0.01 milligrams per liter to 10.0 milligrams per liter.

16. A method of detecting ozone in a fluid, comprising the steps of solubilizing a para-substituted phenylene ring compound where the substituent moieties are selected from the group consisting of five and six membered aminoalkyl rings and five and six membered alkyl rings in said fluid and monitoring a color change in said fluid.

17. A method as recited in claim 16 wherein said step of monitoring further includes the steps of measuring an intensity of a blue color in said fluid and determining a concentration of ozone from said intensity.

18. A method as recited in claim 17 wherein said step of measuring is performed detecting light absorption at 615 nm.

19. A method as recited in claim 16 wherein said step of monitoring is performed by comparing a color observed in said fluid with a color chart.

20. A method as recited in claim 16 wherein said para-substituted phenylene ring compound solubilized in said fluid is selected from the group consisting of 1,1'-para-phenylene dipiperidine and 1,1'-para-phenylene dipyrolidine.

21. A method as recited in claim 20 wherein said para-substituted phenylene ring compound has a concentration ranging from 100 milligrams per liter to 1000 milligrams per liter.

22. A method as recited in claim 21 wherein said concentration is approximately 500 milligrams per liter.

23. A method as recited in claim 20 wherein said para-substituted phenylene ring compound is solubilized as a salt.

24. A method as recited in claim 23 wherein said salt is a hydrochloride salt.

25. A method as recited in claim 23 wherein said salt is a mono-N-alkyl salt.

26. A method as recited in claim 20 wherein said step of monitoring includes the steps of measuring an intensity of a blue color in said fluid and determining a concentration of ozone from said intensity.

27. A method as recited in claim 26 wherein said step of measuring is performed detecting light absorption at 615 nm.

28. A method as recited in claim 26 wherein said concentration of ozone ranges from 0.01 milligrams per liter to 2.5 milligrams per liter.

29. A method for detecting chlorine in a fluid comprising the step of providing a quantity of 1,1'-para-phenylene dipiperidine in said fluid and monitoring for a change in color of said fluid.

30. A method as recited in claim 29 wherein said 1,1'-para-phenylene dipiperidine is provided as its hydrochloride salt.

31. A method for detecting ozone in a fluid comprising the step of providing a quantity of 1,1'-para-phenylene dipyrolidine in said fluid and monitoring for a change in color of said fluid.

32. A method as recited in claim 31 wherein said 1,1'-para-phenylene dipyrolidine is provided as its hydrochloride salt.

33. A method of detecting various chlorine or ozone-containing water-treating agents in a fluid, comprising the steps of solubilizing a para-substituted phenylene ring compound where the substituent moieties are selected from the group consisting of five and six membered aminoalkyl rings and five and six membered alkyl rings in said fluid and monitoring a color change in said fluid.

* * * * *